US008636761B2

(12) United States Patent
Cunningham et al.

(10) Patent No.: US 8,636,761 B2
(45) **Date of Patent: *Jan. 28, 2014**

(54) APPARATUS, SYSTEM, AND METHOD FOR PERFORMING AN ENDOSCOPIC ELECTROSURGICAL PROCEDURE

(75) Inventors: James S. Cunningham, Boulder, CO (US); James D. Allen, IV, Broomfield, CO (US); Edward M. Chojin, Boulder, CO (US)

(73) Assignee: Covidien LP, Mansfield, MA (US)

( * ) Notice: Subject to any disclaimer, the term of this patent is extended or adjusted under 35 U.S.C. 154(b) by 1037 days.

This patent is subject to a terminal disclaimer.

(21) Appl. No.: 12/248,115

(22) Filed: Oct. 9, 2008

(65) Prior Publication Data

US 2010/0094287 A1 Apr. 15, 2010

(51) Int. Cl.
*A61B 17/00* (2006.01)

(52) U.S. Cl.
USPC .......... 606/206

(58) Field of Classification Search
USPC .......... 606/45, 48, 49, 50, 51, 52, 205, 206, 606/207, 208, 209
See application file for complete search history.

(56) References Cited

U.S. PATENT DOCUMENTS

| | | | |
|---|---|---|---|
| 371,664 | A | 10/1887 | Brannan et al. |
| 702,472 | A | 6/1902 | Pignolet |
| 728,883 | A | 5/1903 | Downes |
| 1,586,645 | A | 6/1926 | Bierman |
| 1,813,902 | A | 7/1931 | Bovie |
| 1,822,330 | A | 9/1931 | Ainslie |
| 1,852,542 | A | 4/1932 | Sovatkin |
| 2,002,594 | A | 5/1935 | Wappler et al. |
| 2,011,169 | A | 8/1935 | Wappler |
| 2,031,682 | A | 2/1936 | Wappler et al. |
| 2,054,149 | A | 9/1936 | Wappler |
| 2,176,479 | A | 10/1939 | Willis |

(Continued)

FOREIGN PATENT DOCUMENTS

| | | |
|---|---|---|
| CA | 2104423 | 2/1994 |
| DE | 2415263 | 10/1975 |

(Continued)

OTHER PUBLICATIONS

Michael Choti, "Abdominoperineal Resection with the LigaSure Vessel Sealing System and LigaSure Atlas 20 cm Open Instrument"; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.

(Continued)

*Primary Examiner* — Kevin C Sirmons
*Assistant Examiner* — William Carpenter

(57) ABSTRACT

A bipolar forceps is provided and includes a housing having a shaft that extends therefrom. The housing includes a drive assembly operable to reciprocate an actuation tube within the shaft. An end effector assembly operatively connects to a distal end of the shaft and includes a pair of first and second jaw members biased in an open configuration. One or both of the first and second jaw members is pivotable about a living hinge from a first position to a clamping position. One or both of the jaw members includes a cam slot defined at a proximal end thereof. One of the jaw members is operatively connected to a distal end of the actuation tube via a cam pin that operatively engages the cam slot such that proximal reciprocation of the actuation tube cams at least one jaw member towards the other jaw member about the living hinge.

10 Claims, 5 Drawing Sheets

(56) References Cited

U.S. PATENT DOCUMENTS 2,305,156 A 4/1941 Grubel
2,279,753 A 4/1942 Knopp
2,327,353 A 8/1943 Karle
2,632,661 A 8/1948 Cristofv
2,668,538 A 2/1954 Baker
2,796,065 A 6/1957 Kapp
3,073,311 A 1/1963 Tibbs et al.
3,372,288 A 3/1968 Wigington
3,459,187 A 8/1969 Pallotta
3,643,663 A 2/1972 Sutter
3,648,001 A 3/1972 Anderson et al.
3,651,811 A 3/1972 Hildebrandt et al.
3,678,229 A 7/1972 Osika
3,720,896 A 3/1973 Beierlein
3,763,726 A 10/1973 Hildebrand
3,779,918 A 12/1973 Ikeda et al.
3,801,766 A 4/1974 Morrison, Jr.
3,862,630 A 1/1975 Balamuth
3,863,339 A 2/1975 Reaney et al.
3,866,610 A 2/1975 Kletschka
3,911,766 A 10/1975 Fridolph et al.
3,920,021 A 11/1975 Hiltebrandt
3,921,641 A 11/1975 Hulka
3,938,527 A 2/1976 Rioux et al.
3,952,749 A 4/1976 Fridolph et al.
3,970,088 A 7/1976 Morrison
3,987,795 A 10/1976 Morrison
4,005,714 A 2/1977 Hiltebrandt
4,016,881 A 4/1977 Rioux et al.
4,041,952 A 8/1977 Morrison, Jr. et al.
4,043,342 A 8/1977 Morrison, Jr.
4,074,718 A 2/1978 Morrison, Jr.
4,076,028 A 2/1978 Simmons
4,080,820 A 3/1978 Allen
4,088,134 A 5/1978 Mazzariello
4,112,950 A 9/1978 Pike
4,127,222 A 11/1978 Adams
4,128,099 A 12/1978 Bauer
4,165,746 A 8/1979 Burgin
4,187,420 A 2/1980 Piber
4,233,734 A 11/1980 Bies
4,236,470 A 12/1980 Stenson
4,300,564 A 11/1981 Furihata
4,311,145 A 1/1982 Esty et al.
D263,020 S 2/1982 Rau, III
4,370,980 A 2/1983 Lottick
4,375,218 A 3/1983 DiGeronimo
4,416,276 A 11/1983 Newton et al.
4,418,692 A 12/1983 Guay
4,443,935 A 4/1984 Zamba et al.
4,452,246 A 6/1984 Bader et al.
4,470,786 A 9/1984 Sano et al.
4,492,231 A 1/1985 Auth
4,493,320 A 1/1985 Treat
4,503,855 A 3/1985 Maslanka
4,506,669 A 3/1985 Blake, III
4,509,518 A 4/1985 McGarry et al.
4,552,143 A 11/1985 Lottick
4,574,804 A 3/1986 Kurwa
4,597,379 A 7/1986 Kihn et al.
4,600,007 A 7/1986 Lahodny et al.
4,624,254 A 11/1986 McGarry et al.
4,655,215 A 4/1987 Pike
4,655,216 A 4/1987 Tischer
4,657,016 A 4/1987 Garito et al.
4,662,372 A 5/1987 Sharkany et al.
4,671,274 A 6/1987 Sorochenko
4,685,459 A 8/1987 Xoch et al.
4,733,662 A 3/1988 DeSatnick et al.
D295,893 S 5/1988 Sharkany et al.
D295,894 S 5/1988 Sharkany et al.
4,753,235 A * 6/1988 Hasson ........................ 606/206
4,754,892 A 7/1988 Retief
4,763,669 A 8/1988 Jaeger
4,827,929 A 5/1989 Hodge
4,829,313 A 5/1989 Taggart
4,846,171 A 7/1989 Kauphusman et al.
4,887,612 A 12/1989 Esser et al.
4,938,761 A 7/1990 Ensslin
4,947,009 A 8/1990 Osika et al.
4,985,030 A 1/1991 Melzer et al.
5,007,908 A 4/1991 Rydell
5,026,370 A 6/1991 Lottick
5,026,371 A 6/1991 Rydell et al.
5,035,695 A 7/1991 Weber, Jr. et al.
5,037,433 A 8/1991 Wilk et al.
5,042,707 A 8/1991 Taheri
5,047,046 A 9/1991 Bodoia
5,052,402 A * 10/1991 Bencini et al. ................ 600/564
5,078,716 A 1/1992 Doll
5,084,057 A 1/1992 Green et al.
5,085,659 A 2/1992 Rydell
5,099,840 A 3/1992 Goble et al.
5,100,430 A 3/1992 Avellanet et al.
5,108,392 A 4/1992 Spingler
5,112,343 A 5/1992 Thornton
5,116,332 A 5/1992 Lottick
5,147,357 A 9/1992 Rose et al.
5,151,102 A 9/1992 Kamiyama et al.
5,151,978 A 9/1992 Bronikowski et al.
5,176,695 A 1/1993 Dulebohn
5,190,541 A 3/1993 Abele et al.
5,196,009 A 3/1993 Kirwan, Jr.
5,197,964 A 3/1993 Parins
5,209,747 A 5/1993 Knoepfler
5,211,655 A * 5/1993 Hasson ........................ 606/205
5,215,101 A 6/1993 Jacobs et al.
5,217,457 A 6/1993 Delahuerga et al.
5,217,458 A 6/1993 Parins
5,217,460 A 6/1993 Knoepfler
5,219,354 A 6/1993 Choudhury et al.
5,238,002 A * 8/1993 Devlin et al. ................ 600/564
5,244,462 A 9/1993 Delahuerga et al.
5,250,047 A 10/1993 Rydell
5,250,056 A * 10/1993 Hasson ........................ 606/151
5,250,063 A 10/1993 Abidin et al.
5,258,001 A 11/1993 Corman
5,258,006 A 11/1993 Rydell et al.
5,261,918 A 11/1993 Phillips et al.
5,275,615 A 1/1994 Rose
5,277,201 A 1/1994 Stern
5,282,799 A 2/1994 Rydell
5,282,800 A 2/1994 Foshee et al.
5,282,826 A 2/1994 Quadri
5,290,286 A 3/1994 Parins
5,300,082 A 4/1994 Sharpe et al.
5,304,203 A 4/1994 El-Mallawany et al.
5,308,353 A 5/1994 Beurrier
5,308,357 A 5/1994 Lichtman
5,313,027 A 5/1994 Inoue et al.
5,314,445 A 5/1994 Degwitz et al.
5,318,589 A 6/1994 Lichtman
5,324,289 A 6/1994 Eggers
D348,930 S 7/1994 Olson
5,326,806 A 7/1994 Yokoshima et al.
5,330,471 A 7/1994 Eggers
5,330,502 A 7/1994 Hassler et al.
5,334,183 A 8/1994 Wuchinich
5,334,215 A 8/1994 Chen
5,336,220 A 8/1994 Ryan et al.
5,336,221 A 8/1994 Anderson
5,342,359 A 8/1994 Rydell
5,342,381 A 8/1994 Tidemand
5,342,393 A 8/1994 Stack
5,344,424 A 9/1994 Roberts et al.
5,350,391 A 9/1994 Iacovelli
5,352,222 A 10/1994 Rydell
5,354,271 A 10/1994 Voda
5,356,408 A 10/1994 Rydell
5,366,477 A 11/1994 LeMarie, III et al.
5,368,600 A 11/1994 Failla et al.
5,374,277 A 12/1994 Hassler
5,376,089 A 12/1994 Smith
5,383,875 A 1/1995 Bays et al.

(56) References Cited

U.S. PATENT DOCUMENTS 5,383,897 A 1/1995 Wholey
5,389,098 A 2/1995 Tsuruta et al.
5,389,103 A 2/1995 Melzer et al.
5,389,104 A 2/1995 Hahnen et al.
5,391,166 A 2/1995 Eggers
5,391,183 A 2/1995 Janzen et al.
5,396,900 A 3/1995 Slater et al.
5,403,312 A 4/1995 Yates et al.
5,403,342 A 4/1995 Tovey et al.
5,405,344 A 4/1995 Williamson et al.
5,409,763 A 4/1995 Serizawa et al.
5,411,519 A 5/1995 Tovey et al.
5,411,520 A 5/1995 Nash et al.
5,413,571 A 5/1995 Katsaros et al.
5,415,656 A 5/1995 Tihon et al.
5,415,657 A 5/1995 Taymor-Luria
5,422,567 A 6/1995 Matsunaga
5,423,810 A 6/1995 Goble et al.
5,425,690 A 6/1995 Chang
5,425,739 A 6/1995 Jessen
5,429,616 A 7/1995 Schaffer
5,431,672 A 7/1995 Cote et al.
5,431,674 A 7/1995 Basile et al.
5,437,292 A 8/1995 Kipshidze et al.
5,438,302 A 8/1995 Goble
5,439,478 A 8/1995 Palmer
5,441,517 A 8/1995 Kensey et al.
5,443,463 A 8/1995 Stern et al.
5,443,464 A 8/1995 Russell et al.
5,443,480 A 8/1995 Jacobs et al.
5,445,638 A 8/1995 Rydell et al.
5,445,658 A 8/1995 Durrfeld et al.
5,449,480 A 9/1995 Kuriya et al.
5,451,224 A 9/1995 Goble et al.
5,454,823 A 10/1995 Richardson et al.
5,454,827 A 10/1995 Aust et al.
5,456,684 A 10/1995 Schmidt et al.
5,458,598 A 10/1995 Feinberg et al.
5,460,629 A 10/1995 Shlain et al.
5,461,765 A 10/1995 Linden et al.
5,462,546 A 10/1995 Rydell
5,471,992 A * 12/1995 Banik et al. .................. 600/564
5,472,442 A 12/1995 Klicek
5,472,443 A 12/1995 Cordis et al.
5,478,347 A * 12/1995 Aranyi .......................... 606/170
5,478,351 A 12/1995 Meade et al.
5,480,406 A 1/1996 Nolan et al.
5,480,409 A 1/1996 Riza
5,484,436 A 1/1996 Eggers et al.
5,496,312 A 3/1996 Klicek
5,496,317 A 3/1996 Goble et al.
5,496,347 A 3/1996 Hashiguchi et al.
5,499,997 A 3/1996 Sharpe et al.
5,509,922 A 4/1996 Aranyi et al.
5,512,721 A 4/1996 Young et al.
5,514,134 A 5/1996 Rydell et al.
5,527,313 A * 6/1996 Scott et al. ...................... 606/51
5,528,833 A 6/1996 Sakuma
5,529,067 A 6/1996 Larsen et al.
5,531,744 A 7/1996 Nardella et al.
5,536,251 A 7/1996 Evard et al.
5,540,684 A 7/1996 Hassler, Jr.
5,540,685 A 7/1996 Parins et al.
5,540,706 A 7/1996 Aust et al.
5,540,715 A 7/1996 Katsaros et al.
5,542,945 A 8/1996 Fritzsch
5,558,671 A 9/1996 Yates
5,558,672 A 9/1996 Edwards et al.
5,562,619 A 10/1996 Mirarchi et al.
5,562,699 A 10/1996 Heimberger et al.
5,562,720 A 10/1996 Stern et al.
5,564,615 A 10/1996 Bishop et al.
5,569,241 A 10/1996 Edwardds
5,569,243 A 10/1996 Kortenbach et al.
5,571,100 A 11/1996 Goble et al.
5,573,424 A 11/1996 Poppe
5,573,534 A 11/1996 Stone
5,573,535 A 11/1996 Viklund
5,575,799 A 11/1996 Bolanos et al.
5,575,805 A 11/1996 Li
5,578,052 A 11/1996 Koros et al.
5,579,781 A 12/1996 Cooke
5,582,611 A 12/1996 Tsukagoshi et al.
5,582,617 A 12/1996 Klieman et al.
5,585,896 A 12/1996 Yamazaki et al.
5,590,570 A 1/1997 LeMaire, III et al.
5,591,181 A 1/1997 Stone et al.
5,597,107 A 1/1997 Knodel et al.
5,601,224 A 2/1997 Bishop et al.
5,601,601 A 2/1997 Tal et al.
5,601,641 A 2/1997 Stephens
5,603,711 A 2/1997 Parins et al.
5,603,723 A 2/1997 Aranyi et al.
5,611,798 A 3/1997 Eggers
5,611,808 A 3/1997 Hossain et al.
5,611,813 A 3/1997 Lichtman
5,620,415 A 4/1997 Lucey et al.
5,620,453 A 4/1997 Nallakrishnan
5,620,459 A 4/1997 Lichtman
5,624,452 A 4/1997 Yates
5,626,578 A 5/1997 Tihon
5,626,609 A 5/1997 Zvenyatsky et al.
5,630,833 A 5/1997 Katsaros et al.
5,637,110 A 6/1997 Pennybacker et al.
5,638,003 A 6/1997 Hall
5,643,294 A 7/1997 Tovey et al.
5,647,869 A 7/1997 Goble et al.
5,647,871 A 7/1997 Levine et al.
5,649,959 A 7/1997 Hannam et al.
5,655,650 A 8/1997 Naitou
5,658,281 A 8/1997 Heard
D384,413 S 9/1997 Zlock et al.
5,662,667 A 9/1997 Knodel
5,665,100 A 9/1997 Yoon
5,667,526 A 9/1997 Levin
5,674,220 A 10/1997 Fox et al.
5,674,229 A 10/1997 Tovey et al.
5,681,282 A 10/1997 Eggers et al.
5,688,270 A 11/1997 Yates et al.
5,690,652 A 11/1997 Wurster et al.
5,690,653 A 11/1997 Richardson et al.
5,693,051 A 12/1997 Schulze et al.
5,693,920 A 12/1997 Maeda
5,695,522 A 12/1997 LeMaire, III et al.
5,700,261 A 12/1997 Brinkerhoff
5,700,270 A 12/1997 Peyser et al.
5,702,390 A 12/1997 Austin et al.
5,707,369 A 1/1998 Vaitekunas et al.
5,709,680 A 1/1998 Yates et al.
5,716,366 A 2/1998 Yates
5,720,744 A 2/1998 Eggleston et al.
5,722,421 A 3/1998 Francese et al.
5,725,536 A 3/1998 Oberlin et al.
5,727,428 A 3/1998 LeMaire, III et al.
5,735,848 A 4/1998 Yates et al.
5,743,906 A 4/1998 Parins et al.
5,752,973 A * 5/1998 Kieturakis .................... 606/207
5,755,717 A 5/1998 Yates et al.
5,759,188 A 6/1998 Yoon
5,766,130 A 6/1998 Selmonosky
5,766,166 A 6/1998 Hooven
5,766,170 A 6/1998 Eggers
5,766,196 A 6/1998 Griffiths
5,769,849 A 6/1998 Eggers
5,772,655 A 6/1998 Bauer et al.
5,772,670 A 6/1998 Brosa
5,776,128 A 7/1998 Eggers
5,776,130 A 7/1998 Buysse et al.
5,779,646 A 7/1998 Koblish et al.
5,779,701 A 7/1998 McBrayer et al.
H1745 H 8/1998 Paraschac
5,792,137 A 8/1998 Carr et al.
5,792,165 A 8/1998 Klieman et al.
5,792,177 A 8/1998 Kaseda

(56) References Cited

U.S. PATENT DOCUMENTS 5,797,537 A 8/1998 Oberlin et al.
5,797,927 A 8/1998 Yoon
5,797,938 A 8/1998 Paraschac et al.
5,797,941 A 8/1998 Schulze et al.
5,797,958 A 8/1998 Yoon
5,800,449 A 9/1998 Wales
5,807,393 A 9/1998 Williamson, IV et al.
5,810,764 A 9/1998 Eggers et al.
5,810,805 A 9/1998 Sutcu et al.
5,810,808 A 9/1998 Eggers
5,810,811 A 9/1998 Yates et al.
5,810,877 A 9/1998 Roth et al.
5,814,043 A 9/1998 Shapeton
5,814,054 A * 9/1998 Kortenbach et al. .......... 606/139
5,817,093 A 10/1998 Williamson, IV et al.
5,817,119 A 10/1998 Klieman et al.
5,820,630 A 10/1998 Lind
5,824,978 A 10/1998 Karasik et al.
5,827,271 A 10/1998 Buysse et al.
5,827,279 A 10/1998 Hughett et al.
5,827,281 A 10/1998 Levin
5,827,323 A 10/1998 Klieman et al.
5,827,548 A 10/1998 Lavallee et al.
5,833,690 A 11/1998 Yates et al.
5,843,080 A 12/1998 Fleenor et al.
5,849,022 A 12/1998 Sakashita et al.
5,853,412 A 12/1998 Mayenberger
5,859,527 A 1/1999 Cook
5,860,976 A 1/1999 Billings et al.
5,876,401 A 3/1999 Schulze et al.
5,876,412 A 3/1999 Piraka
5,882,567 A 3/1999 Cavallaro et al.
5,891,141 A 4/1999 Rydell
5,891,142 A 4/1999 Eggers et al.
5,893,863 A 4/1999 Yoon
5,893,875 A 4/1999 O'Connor et al.
5,893,877 A 4/1999 Gampp, Jr. et al.
5,897,563 A 4/1999 Yoon et al.
5,902,301 A 5/1999 Olig
5,906,630 A 5/1999 Anderhub et al.
5,908,420 A 6/1999 Parins et al.
5,908,432 A 6/1999 Pan
5,911,719 A 6/1999 Eggers
5,913,874 A 6/1999 Berns et al.
5,921,916 A 7/1999 Aeikens et al.
5,921,984 A 7/1999 Sutcu et al.
5,925,043 A 7/1999 Kumar et al.
5,928,136 A 7/1999 Barry
5,935,126 A 8/1999 Riza
5,941,869 A 8/1999 Patterson et al.
5,944,718 A 8/1999 Dafforn et al.
5,951,546 A 9/1999 Lorentzen
5,951,549 A 9/1999 Richardson et al.
5,954,720 A 9/1999 Wilson et al.
5,954,731 A 9/1999 Yoon
5,954,733 A 9/1999 Yoon
5,957,923 A 9/1999 Hahnen et al.
5,957,937 A 9/1999 Yoon
5,960,544 A 10/1999 Beyers
5,961,514 A 10/1999 Long et al.
5,964,758 A 10/1999 Dresden
5,976,132 A 11/1999 Morris
5,984,932 A 11/1999 Yoon
5,984,938 A 11/1999 Yoon
5,984,939 A 11/1999 Yoon
5,989,277 A 11/1999 LeMaire, III et al.
5,993,466 A 11/1999 Yoon
5,993,467 A 11/1999 Yoon
5,993,474 A * 11/1999 Ouchi .......................... 606/206
5,997,565 A 12/1999 Inoue
6,004,332 A 12/1999 Yoon et al.
6,004,335 A 12/1999 Vaitekunas et al.
6,010,516 A 1/2000 Hulka et al.
6,017,358 A 1/2000 Yoon et al.
6,021,693 A 2/2000 Feng-Sing
6,024,741 A 2/2000 Williamson et al.
6,024,743 A 2/2000 Edwards
6,024,744 A 2/2000 Kese et al.
6,027,522 A 2/2000 Palmer
6,030,384 A 2/2000 Nezhat
6,033,399 A 3/2000 Gines
6,039,733 A 3/2000 Buysse et al.
6,041,679 A 3/2000 Slater et al.
6,050,996 A 4/2000 Schmaltz et al.
6,053,914 A 4/2000 Eggers et al.
6,053,933 A 4/2000 Balazs et al.
D424,694 S 5/2000 Tetzlaff et al.
D425,201 S 5/2000 Tetzlaff et al.
6,059,782 A 5/2000 Novak et al.
6,066,139 A 5/2000 Ryan et al.
6,074,386 A 6/2000 Goble et al.
6,077,287 A 6/2000 Taylor et al.
6,080,180 A 6/2000 Yoon et al.
RE36,795 E 7/2000 Rydell
6,083,223 A 7/2000 Baker
6,086,586 A 7/2000 Hooven
6,086,601 A 7/2000 Yoon
6,090,107 A 7/2000 Borgmeier et al.
6,096,037 A 8/2000 Mulier et al.
6,099,550 A 8/2000 Yoon
6,102,909 A 8/2000 Chen et al.
6,106,542 A 8/2000 Toybin et al.
6,110,171 A 8/2000 Rydell
6,113,596 A 9/2000 Hooven et al.
6,113,598 A * 9/2000 Baker ............................ 606/51
6,117,158 A 9/2000 Measamer et al.
6,122,549 A 9/2000 Sharkey et al.
6,123,701 A 9/2000 Nezhat
H1904 H 10/2000 Yates et al.
6,126,658 A 10/2000 Baker
6,126,665 A 10/2000 Yoon
6,139,563 A 10/2000 Cosgrove, III et al.
6,143,005 A 11/2000 Yoon et al.
6,152,923 A 11/2000 Ryan
6,162,220 A 12/2000 Nezhat
6,171,316 B1 1/2001 Kovac et al.
6,174,309 B1 1/2001 Wrublewski et al.
6,178,628 B1 1/2001 Clemens et al.
6,179,834 B1 1/2001 Buysse et al.
6,179,837 B1 1/2001 Hooven
6,183,467 B1 2/2001 Shapeton et al.
6,187,003 B1 2/2001 Buysse et al.
6,190,386 B1 2/2001 Rydell
6,190,400 B1 2/2001 Vandemoer et al.
6,193,718 B1 2/2001 Kortenbach et al.
6,206,876 B1 3/2001 Levine et al.
6,206,877 B1 3/2001 Kese et al.
6,206,893 B1 3/2001 Klein et al.
6,214,028 B1 4/2001 Yoon et al.
6,217,602 B1 4/2001 Redmon
6,217,615 B1 4/2001 Sioshansi et al.
6,221,039 B1 4/2001 Durgin et al.
6,223,100 B1 4/2001 Green
6,224,593 B1 5/2001 Ryan et al.
6,224,614 B1 5/2001 Yoon
6,228,080 B1 5/2001 Gines
6,228,083 B1 * 5/2001 Lands et al. .................... 606/50
6,248,124 B1 6/2001 Pedros et al.
6,248,944 B1 6/2001 Ito
6,261,307 B1 7/2001 Yoon et al.
6,267,761 B1 7/2001 Ryan
6,270,497 B1 8/2001 Sekino et al.
6,270,508 B1 8/2001 Klieman et al.
6,273,887 B1 8/2001 Yamauchi et al.
6,277,117 B1 8/2001 Tetzlaff et al.
6,280,458 B1 8/2001 Boche et al.
6,283,961 B1 9/2001 Underwood et al.
D449,886 S 10/2001 Tetzlaff et al.
6,298,550 B1 10/2001 Kirwan
6,302,424 B1 10/2001 Gisinger et al.
6,319,262 B1 11/2001 Bates et al.
6,319,451 B1 11/2001 Brune
6,322,561 B1 11/2001 Eggers et al.
6,322,580 B1 11/2001 Kanner

(56) References Cited

U.S. PATENT DOCUMENTS 6,325,795 B1 12/2001 Lindemann et al.
6,334,860 B1 1/2002 Dorn
6,334,861 B1 1/2002 Chandler et al.
6,345,532 B1 2/2002 Coudray et al.
6,350,264 B1 2/2002 Hooven
6,352,536 B1 3/2002 Buysse et al.
6,358,249 B1 3/2002 Chen et al.
6,358,259 B1 3/2002 Swain et al.
6,358,268 B1 3/2002 Hunt et al.
6,364,879 B1 4/2002 Chen et al.
D457,958 S 5/2002 Dycus et al.
D457,959 S 5/2002 Tetzlaff et al.
6,387,094 B1 5/2002 Eitenmuller
6,391,035 B1 5/2002 Appleby et al.
6,398,779 B1 6/2002 Buysse et al.
6,402,747 B1 6/2002 Lindemann et al.
6,409,728 B1 6/2002 Ehr et al.
H2037 H 7/2002 Yates et al.
6,419,675 B1 7/2002 Gallo, Sr.
6,425,896 B1 7/2002 Baltschun et al.
6,432,112 B2 8/2002 Brock et al.
6,440,144 B1 8/2002 Bacher
6,443,952 B1 9/2002 Mulier et al.
6,443,970 B1 9/2002 Schulze et al.
6,451,018 B1 9/2002 Lands et al.
6,458,125 B1 10/2002 Cosmescu
6,458,128 B1 10/2002 Schulze
6,458,130 B1 10/2002 Frazier et al.
6,461,352 B2 10/2002 Morgan et al.
6,461,368 B2 10/2002 Fogarty et al.
6,464,701 B1 10/2002 Hooven et al.
6,464,702 B2 10/2002 Schulze et al.
6,464,704 B2 10/2002 Schmaltz et al.
6,485,489 B2 11/2002 Teirstein et al.
6,494,888 B1 12/2002 Laufer et al.
6,500,176 B1 12/2002 Truckai et al.
6,506,196 B1 1/2003 Laufer
6,508,815 B1 1/2003 Strul et al.
6,511,480 B1 1/2003 Tetzlaff et al.
6,514,215 B1 2/2003 Ouchi
6,514,252 B2 2/2003 Nezhat et al.
6,517,539 B1 2/2003 Smith et al.
6,527,771 B1 3/2003 Weadock et al.
6,533,784 B2 3/2003 Truckai et al.
6,545,239 B2 4/2003 Spedale et al.
6,558,385 B1 5/2003 McClurken et al.
6,562,037 B2 5/2003 Paton et al.
6,569,105 B1 5/2003 Kortenbach et al.
6,582,450 B2 6/2003 Ouchi
6,585,735 B1 7/2003 Frazier et al.
6,602,252 B2 8/2003 Mollenauer
6,605,790 B2 8/2003 Yoshida
6,616,658 B2 9/2003 Ineson
6,616,661 B2 9/2003 Wellman et al.
6,620,161 B2 9/2003 Schulze et al.
6,620,184 B2 9/2003 de Laforcade et al.
6,626,901 B1 9/2003 Treat et al.
6,638,287 B2 10/2003 Danitz et al.
6,641,595 B1 11/2003 Moran et al.
6,652,514 B2 11/2003 Ellman et al.
6,652,521 B2 11/2003 Schulze
6,656,175 B2 12/2003 Francischelli et al.
6,656,177 B2 12/2003 Truckai et al.
6,660,072 B2 12/2003 Chatterjee
6,663,639 B1 12/2003 Laufer et al.
6,663,641 B1 12/2003 Kovac et al.
6,666,854 B1 12/2003 Lange
6,669,696 B2 12/2003 Bacher et al.
6,673,092 B1 1/2004 Bacher
6,676,660 B2 1/2004 Wampler et al.
6,676,676 B2 1/2004 Danitz et al.
6,679,882 B1 1/2004 Kornerup
6,682,527 B2 1/2004 Strul
6,682,528 B2 1/2004 Frazier et al.
6,685,724 B1 2/2004 Haluck
6,689,131 B2 2/2004 McClurken
6,692,445 B2 2/2004 Roberts et al.
6,693,246 B1 2/2004 Rudolph et al.
6,695,840 B2 2/2004 Schulze
6,702,810 B2 3/2004 McClurken et al.
6,723,092 B2 4/2004 Brown et al.
6,726,068 B2 4/2004 Miller
6,726,686 B2 4/2004 Buysse et al.
6,726,694 B2 4/2004 Blatter et al.
6,733,498 B2 5/2004 Paton et al.
6,736,813 B2 5/2004 Yamauchi et al.
6,743,229 B2 6/2004 Buysse et al.
6,743,230 B2 6/2004 Lutze et al.
6,743,239 B1 6/2004 Kuehn et al.
6,743,240 B2 6/2004 Smith et al.
6,755,843 B2 6/2004 Chung et al.
6,756,553 B1 6/2004 Yamaguchi et al.
6,757,977 B2 7/2004 Dambal et al.
D493,888 S 8/2004 Reschke
6,770,072 B1 8/2004 Truckai et al.
6,773,409 B2 8/2004 Truckai et al.
6,773,432 B1 8/2004 Clayman et al.
6,773,434 B2 8/2004 Ciarrocca
6,773,441 B1 8/2004 Laufer et al.
6,775,575 B2 8/2004 Bommannan et al.
6,776,780 B2 8/2004 Mulier et al.
6,786,905 B2 9/2004 Swanson et al.
6,790,217 B2 9/2004 Schulze et al.
6,796,981 B2 9/2004 Wham et al.
D496,997 S 10/2004 Dycus et al.
6,800,825 B1 10/2004 Sasaki et al.
6,802,843 B2 10/2004 Truckai et al.
6,808,525 B2 10/2004 Latterell et al.
D499,181 S 11/2004 Dycus et al.
6,818,000 B2 11/2004 Muller et al.
6,821,285 B2 11/2004 Laufer et al.
6,835,200 B2 12/2004 Laufer et al.
6,857,357 B2 2/2005 Fujii
6,860,880 B2 3/2005 Treat et al.
6,887,240 B1 5/2005 Lands et al.
6,889,116 B2 5/2005 Jinno
6,914,201 B2 7/2005 Van Vooren et al.
6,926,716 B2 8/2005 Baker et al.
6,929,644 B2 8/2005 Truckai et al.
6,932,810 B2 8/2005 Ryan
6,932,816 B2 8/2005 Phan
6,934,134 B2 8/2005 Mori et al.
6,936,061 B2 8/2005 Sasaki
D509,297 S 9/2005 Wells
6,942,662 B2 9/2005 Goble et al.
6,943,311 B2 9/2005 Miyako
6,953,430 B2 10/2005 Kodooka
6,953,461 B2 10/2005 McClurken et al.
6,958,070 B2 10/2005 Witt et al.
6,960,210 B2 11/2005 Lands et al.
6,964,662 B2 11/2005 Kidooka
6,966,907 B2 11/2005 Goble
6,972,017 B2 12/2005 Smith et al.
6,977,495 B2 12/2005 Donofrio
6,979,786 B2 12/2005 Aukland et al.
6,981,628 B2 1/2006 Wales
6,987,244 B2 1/2006 Bauer
6,994,707 B2 2/2006 Ellman et al.
6,994,709 B2 2/2006 Iida
6,997,931 B2 2/2006 Sauer et al.
7,001,381 B2 2/2006 Harano et al.
7,011,657 B2 3/2006 Truckai et al.
7,033,354 B2 4/2006 Keppel
7,033,356 B2 4/2006 Latterell et al.
7,041,102 B2 5/2006 Truckai et al.
7,044,948 B2 5/2006 Keppel
7,052,489 B2 5/2006 Griego et al.
7,052,496 B2 5/2006 Yamauchi
7,063,715 B2 6/2006 Onuki et al.
D525,361 S 7/2006 Hushka
7,070,597 B2 7/2006 Truckai et al.
7,083,618 B2 8/2006 Couture et al.
7,083,619 B2 8/2006 Truckai et al.
7,083,620 B2 8/2006 Jahns et al.

(56) References Cited

U.S. PATENT DOCUMENTS 7,087,051 B2 8/2006 Bourne et al.
7,087,054 B2 8/2006 Truckai et al.
7,090,673 B2 8/2006 Dycus et al.
7,090,689 B2 8/2006 Nagase et al.
7,101,371 B2 9/2006 Dycus et al.
7,101,372 B2 9/2006 Dycus et al.
7,101,373 B2 9/2006 Dycus et al.
7,103,947 B2 9/2006 Sartor et al.
7,107,124 B2 9/2006 Green
7,112,199 B2 9/2006 Cosmescu
D531,311 S 10/2006 Guerra et al.
7,115,123 B2 10/2006 Knowlton et al.
7,118,570 B2 10/2006 Tetzlaff et al.
7,118,587 B2 10/2006 Dycus et al.
7,131,860 B2 11/2006 Sartor et al.
7,131,970 B2 11/2006 Moses et al.
7,131,971 B2 11/2006 Dycus et al.
7,135,020 B2 11/2006 Lawes et al.
D533,942 S 12/2006 Kerr et al.
7,145,757 B2 12/2006 Shea et al.
7,147,638 B2 12/2006 Chapman et al.
7,150,097 B2 12/2006 Sremcich et al.
7,150,749 B2 12/2006 Dycus et al.
7,153,314 B2 12/2006 Laufer et al.
D535,027 S 1/2007 James et al.
7,156,842 B2 1/2007 Sartor et al.
7,156,846 B2 1/2007 Dycus et al.
7,160,298 B2 1/2007 Lawes et al.
7,160,299 B2 1/2007 Baily
7,169,146 B2 1/2007 Truckai et al.
7,179,255 B2 2/2007 Lettice et al.
7,179,258 B2 2/2007 Buysse et al.
7,195,631 B2 3/2007 Dumbauld
D541,418 S 4/2007 Schechter et al.
7,207,990 B2 4/2007 Lands et al.
D541,938 S 5/2007 Kerr et al
7,223,264 B2 5/2007 Daniel et al.
7,223,265 B2 5/2007 Keppel
7,232,440 B2 6/2007 Dumbauld et al.
7,241,288 B2 7/2007 Braun
7,241,296 B2 7/2007 Buysse et al.
7,244,257 B2 7/2007 Podjahsky et al.
7,246,734 B2 7/2007 Shelto, IV
7,248,944 B2 7/2007 Green
7,252,667 B2 8/2007 Moses et al.
7,255,697 B2 8/2007 Dycus et al.
7,267,677 B2 9/2007 Johnson et al.
7,270,660 B2 9/2007 Ryan
7,270,664 B2 9/2007 Johnson et al.
7,276,068 B2 10/2007 Johnson et al.
7,300,435 B2 11/2007 Wham et al.
7,303,557 B2 12/2007 Wham et al.
7,311,709 B2 12/2007 Truckai et al.
7,314,471 B2 1/2008 Holman
7,318,823 B2 1/2008 Sharps et al.
7,329,256 B2 2/2008 Johnson et al.
7,329,257 B2 2/2008 Kanehira et al.
D564,662 S 3/2008 Moses et al.
7,338,526 B2 3/2008 Steinberg
7,342,754 B2 3/2008 Fitzgerald et al.
7,344,268 B2 3/2008 Jhigamian
D567,943 S 4/2008 Moses et al.
7,367,976 B2 5/2008 Lawes et al.
7,377,920 B2 * 5/2008 Buysse et al. .................. 606/50
7,384,420 B2 6/2008 Dycus et al.
7,384,421 B2 6/2008 Hushka
7,396,336 B2 7/2008 Orszulak et al.
D575,395 S 8/2008 Hushka
D575,401 S 8/2008 Hixson et al.
7,435,249 B2 10/2008 Buysse et al.
7,442,193 B2 10/2008 Shields et al.
7,442,194 B2 10/2008 Dumbauld et al.
7,445,621 B2 11/2008 Dumbauld et al.
7,458,972 B2 12/2008 Keppel
7,473,253 B2 1/2009 Dycus et al.
7,481,810 B2 1/2009 Dumbauld et al.
7,487,780 B2 2/2009 Hooven
7,491,201 B2 2/2009 Shields et al.
7,491,202 B2 2/2009 Odom et al.
7,500,975 B2 3/2009 Cunningham et al.
7,510,556 B2 3/2009 Nguyen et al.
7,513,898 B2 4/2009 Johnson et al.
7,540,872 B2 6/2009 Schechter et al.
7,549,995 B2 6/2009 Schultz
7,553,312 B2 6/2009 Tetzlaff et al.
7,628,792 B2 * 12/2009 Guerra ........................... 606/51
2002/0013583 A1 1/2002 Camran et al.
2002/0049442 A1 4/2002 Roberts et al.
2002/0099372 A1 7/2002 Schulze et al.
2002/0099375 A1 * 7/2002 Hess et al. ...................... 606/51
2002/0107517 A1 8/2002 Witt et al.
2002/0111624 A1 8/2002 Witt et al.
2002/0188294 A1 * 12/2002 Couture et al. ................. 606/51
2003/0014052 A1 1/2003 Buysse et al.
2003/0014053 A1 1/2003 Nguyen et al.
2003/0018331 A1 1/2003 Dycus et al.
2003/0018332 A1 1/2003 Schmaltz et al.
2003/0032956 A1 2/2003 Lands et al.
2003/0069570 A1 4/2003 Witzel et al.
2003/0069571 A1 4/2003 Treat et al.
2003/0078578 A1 4/2003 Truckai et al.
2003/0109875 A1 6/2003 Tetzlaff et al.
2003/0114851 A1 6/2003 Truckai et al.
2003/0139741 A1 7/2003 Goble et al.
2003/0139742 A1 7/2003 Wampler et al.
2003/0158548 A1 8/2003 Phan et al.
2003/0158549 A1 8/2003 Swanson
2003/0171747 A1 9/2003 Kanehira et al.
2003/0181910 A1 9/2003 Dycus et al.
2003/0191494 A1 * 10/2003 Gray et al. .................... 606/205
2003/0216732 A1 11/2003 Truckai et al.
2003/0220637 A1 11/2003 Truckai et al.
2003/0229344 A1 * 12/2003 Dycus et al. ................... 606/51
2003/0236325 A1 12/2003 Bonora
2003/0236518 A1 12/2003 Marchitto et al.
2004/0030330 A1 2/2004 Brassell et al.
2004/0030332 A1 2/2004 Knowlton et al.
2004/0049185 A1 3/2004 Latterell et al.
2004/0064151 A1 4/2004 Mollenauer
2004/0073238 A1 4/2004 Makower
2004/0073256 A1 4/2004 Marchitto et al.
2004/0078035 A1 4/2004 Kanehira et al.
2004/0082952 A1 4/2004 Dycus et al.
2004/0087943 A1 5/2004 Dycus et al.
2004/0115296 A1 6/2004 Duffin
2004/0116924 A1 6/2004 Dycus et al.
2004/0116979 A1 6/2004 Truckai et al.
2004/0143263 A1 7/2004 Schechter et al.
2004/0148035 A1 7/2004 Barrett et al.
2004/0162557 A1 8/2004 Tetzlaff et al.
2004/0193153 A1 9/2004 Sartor et al.
2004/0199181 A1 10/2004 Knodel et al.
2004/0210282 A1 10/2004 Flock et al.
2004/0224590 A1 11/2004 Rawa et al.
2004/0230189 A1 11/2004 Keppel
2004/0236326 A1 11/2004 Schulze et al.
2004/0243125 A1 12/2004 Dycus et al.
2004/0249374 A1 12/2004 Tetzlaff et al.
2004/0260281 A1 12/2004 Baxter, III et al.
2005/0004564 A1 1/2005 Wham et al.
2005/0004569 A1 1/2005 Witt et al.
2005/0033278 A1 2/2005 McClurken et al.
2005/0059934 A1 3/2005 Wenchell et al.
2005/0096645 A1 5/2005 Wellman et al.
2005/0101951 A1 5/2005 Wham et al.
2005/0101952 A1 5/2005 Lands et al.
2005/0113818 A1 5/2005 Sartor et al.
2005/0113819 A1 5/2005 Wham et al.
2005/0113826 A1 5/2005 Johnson et al.
2005/0149017 A1 7/2005 Dycus
2005/0149151 A1 7/2005 Orszulak et al.
2005/0154387 A1 7/2005 Moses et al.
2005/0187547 A1 8/2005 Sugi
2005/0197659 A1 9/2005 Bahney

(56) References Cited

U.S. PATENT DOCUMENTS

2005/0203504 A1 9/2005 Wham et al.
2006/0052777 A1* 3/2006 Dumbauld ..................... 606/51
2006/0052778 A1 3/2006 Chapman et al.
2006/0052779 A1 3/2006 Hammill
2006/0064085 A1 3/2006 Schechter et al.
2006/0064086 A1 3/2006 Odom
2006/0074417 A1 4/2006 Cunningham et al.
2006/0079888 A1 4/2006 Mulier et al.
2006/0079890 A1 4/2006 Guerra
2006/0079891 A1 4/2006 Arts et al.
2006/0079933 A1 4/2006 Hushka et al.
2006/0084973 A1 4/2006 Hushka
2006/0089670 A1 4/2006 Hushka
2006/0116675 A1 6/2006 McClurken et al.
2006/0129146 A1 6/2006 Dycus et al.
2006/0167450 A1 7/2006 Johnson et al.
2006/0167452 A1 7/2006 Moses et al.
2006/0173452 A1 8/2006 Buysse et al.
2006/0189981 A1 8/2006 Dycus et al.
2006/0190035 A1 8/2006 Hushka et al.
2006/0217709 A1 9/2006 Couture et al.
2006/0229666 A1 10/2006 Suzuki et al.
2006/0253126 A1 11/2006 Bjerken et al.
2006/0259036 A1 11/2006 Tetzlaff et al.
2006/0264922 A1 11/2006 Sartor et al.
2006/0264931 A1 11/2006 Chapman et al.
2006/0283093 A1 12/2006 Petrovic et al.
2006/0287641 A1 12/2006 Perlin
2007/0016182 A1 1/2007 Lipson et al.
2007/0016187 A1 1/2007 Weinberg et al.
2007/0043352 A1 2/2007 Garrison et al.
2007/0043353 A1 2/2007 Dycus et al.
2007/0060919 A1 3/2007 Isaacson et al.
2007/0062017 A1 3/2007 Dycus et al.
2007/0074807 A1 4/2007 Guerra
2007/0078456 A1 4/2007 Dumbauld et al.
2007/0078458 A1 4/2007 Dumbauld et al.
2007/0078459 A1 4/2007 Johnson et al.
2007/0088356 A1 4/2007 Moses et al.
2007/0106295 A1 5/2007 Garrison et al.
2007/0106297 A1 5/2007 Dumbauld et al.
2007/0118111 A1 5/2007 Weinberg
2007/0118115 A1 5/2007 Artale et al.
2007/0142833 A1 6/2007 Dycus et al.
2007/0142834 A1 6/2007 Dumbauld
2007/0156139 A1 7/2007 Schechter et al.
2007/0156140 A1 7/2007 Baily
2007/0173811 A1 7/2007 Couture et al.
2007/0173814 A1 7/2007 Hixson et al.
2007/0179499 A1 8/2007 Garrison
2007/0198011 A1 8/2007 Sugita
2007/0213712 A1 9/2007 Buysse et al.
2007/0255279 A1 11/2007 Buysse et al.
2007/0260235 A1 11/2007 Podhajsky
2007/0260238 A1 11/2007 Guerra
2007/0260241 A1 11/2007 Dalla Betta et al.
2007/0260242 A1 11/2007 Dycus et al.
2007/0265616 A1 11/2007 Couture et al.
2008/0004616 A1 1/2008 Patrick
2008/0009860 A1 1/2008 Odom
2008/0015575 A1 1/2008 Odom et al.
2008/0021450 A1 1/2008 Couture
2008/0033428 A1 2/2008 Artale et al.
2008/0039835 A1 2/2008 Johnson et al.
2008/0039836 A1 2/2008 Odom et al.
2008/0045947 A1 2/2008 Johnson et al.
2008/0058802 A1 3/2008 Couture et al.
2008/0082100 A1 4/2008 Orton et al.
2008/0091189 A1 4/2008 Carlton
2008/0114356 A1 5/2008 Johnson et al.
2008/0167651 A1 7/2008 Tetzlaff et al.
2008/0195093 A1 8/2008 Couture et al.
2008/0215051 A1 9/2008 Buysse et al.
2008/0243120 A1 10/2008 Lawes et al.
2008/0249527 A1 10/2008 Couture
2008/0312653 A1 12/2008 Arts et al.
2008/0319442 A1 12/2008 Unger et al.
2009/0012520 A1 1/2009 Hixson et al.
2009/0018535 A1 1/2009 Schechter et al.
2009/0024126 A1 1/2009 Artale et al.
2009/0043304 A1 2/2009 Tetzlaff et al.
2009/0048596 A1 2/2009 Shields et al.
2009/0062794 A1 3/2009 Buysse et al.
2009/0082766 A1 3/2009 Unger et al.
2009/0082767 A1 3/2009 Unger et al.
2009/0082769 A1 3/2009 Unger et al.
2009/0088738 A1 4/2009 Guerra et al.
2009/0088739 A1 4/2009 Hushka et al.
2009/0088740 A1 4/2009 Guerra et al.
2009/0088741 A1 4/2009 Hushka et al.
2009/0088744 A1 4/2009 Townsend
2009/0088745 A1 4/2009 Hushka et al.
2009/0088746 A1 4/2009 Hushka et al.
2009/0088747 A1 4/2009 Hushka et al.
2009/0088748 A1 4/2009 Guerra et al.
2009/0088749 A1 4/2009 Hushka et al.
2009/0088750 A1 4/2009 Hushka et al.
2009/0112206 A1 4/2009 Dumbauld et al.
2009/0131934 A1 5/2009 Odom et al.
2009/0149853 A1 6/2009 Shields et al.
2009/0149854 A1 6/2009 Cunningham et al.
2009/0171350 A1 7/2009 Dycus et al.
2009/0171353 A1 7/2009 Johnson et al.
2009/0171354 A1* 7/2009 Deville et al. .................. 606/51
2009/0182327 A1 7/2009 Unger
2009/0187188 A1 7/2009 Guerra et al.
2009/0209960 A1* 8/2009 Chojin ........................... 606/51
2012/0232580 A1* 9/2012 Aue ............................. 606/206

FOREIGN PATENT DOCUMENTS

DE 2514501 10/1976
DE 2627679 1/1977
DE 3612646 4/1987
DE 8712328 3/1988
DE 4303882 8/1994
DE 4403252 8/1995
DE 19515914 7/1996
DE 29616210 1/1997
DE 19608716 4/1997
DE 19751106 5/1998
DE 19751108 5/1999
DE 19738457 1/2009
EP 0364216 4/1990
EP 0467501 1/1992
EP 0518230 12/1992
EP 0541930 5/1993
EP 0572131 12/1993
EP 0584787 3/1994
EP 0589453 3/1994
EP 0589555 3/1994
EP 0623316 11/1994
EP 0624348 11/1994
EP 0650701 5/1995
EP 0694290 3/1996
EP 0717966 6/1996
EP 0754437 3/1997
EP 0517243 9/1997
EP 0853922 7/1998
EP 0875209 11/1998
EP 0878169 11/1998
EP 0887046 1/1999
EP 0923907 6/1999
EP 0986990 3/2000
EP 1034747 9/2000
EP 1034748 9/2000
EP 1025807 10/2000
EP 1034746 10/2000
EP 1050278 11/2000
EP 1053719 11/2000
EP 1053720 11/2000
EP 1055399 11/2000
EP 1055400 11/2000
EP 1080694 3/2001

(56) References Cited

FOREIGN PATENT DOCUMENTS

| | | | |
|---|---|---|---|
| EP | 1082944 | | 3/2001 |
| EP | 1159926 | | 12/2001 |
| EP | 1177771 | | 2/2002 |
| EP | 1301135 | | 4/2003 |
| EP | 1330991 | | 7/2003 |
| EP | 1486177 | | 6/2004 |
| EP | 1472984 | | 11/2004 |
| EP | 0774232 | | 1/2005 |
| EP | 1527747 | | 5/2005 |
| EP | 1530952 | | 5/2005 |
| EP | 1532932 | | 5/2005 |
| EP | 1535581 | | 6/2005 |
| EP | 1609430 | | 12/2005 |
| EP | 1632192 | | 3/2006 |
| EP | 1642543 | | 4/2006 |
| EP | 1645238 | | 4/2006 |
| EP | 1645240 | | 4/2006 |
| EP | 1649821 | | 4/2006 |
| EP | 1707143 | | 10/2006 |
| EP | 1769765 | | 4/2007 |
| EP | 1769766 | | 4/2007 |
| EP | 1929970 | | 6/2008 |
| EP | 1683496 | | 12/2008 |
| GB | 623316 | | 5/1949 |
| GB | 1490585 | | 11/1977 |
| GB | 2214430 | A | 6/1989 |
| GB | 2213416 | A | 8/1989 |
| JP | 61-501068 | | 9/1984 |
| JP | 65-502328 | | 3/1992 |
| JP | 5-5106 | | 1/1993 |
| JP | 5-40112 | | 2/1993 |
| JP | 06343644 | A2 | 12/1994 |
| JP | 07265328 | A2 | 10/1995 |
| JP | 08056955 | A2 | 3/1996 |
| JP | 08252263 | A2 | 10/1996 |
| JP | 09010223 | A2 | 1/1997 |
| JP | 11244298 | A2 | 9/1999 |
| JP | 2000-342599 | A2 | 12/2000 |
| JP | 2000-350732 | A2 | 12/2000 |
| JP | 2001-008944 | A2 | 1/2001 |
| JP | 2001-029356 | A2 | 2/2001 |
| JP | 2001-128990 | A2 | 5/2001 |
| SU | 401367 | | 11/1974 |
| WO | WO 89/00757 | | 1/1989 |
| WO | WO 92/04873 | | 4/1992 |
| WO | WO 92/06642 | | 4/1992 |
| WO | WO 93/21845 | | 11/1993 |
| WO | WO 94/08524 | | 4/1994 |
| WO | WO 94/20025 | | 9/1994 |
| WO | WO 95/02369 | | 1/1995 |
| WO | WO 95/07662 | | 3/1995 |
| WO | WO 95/15124 | | 6/1995 |
| WO | WO 96/05776 | | 2/1996 |
| WO | WO 96/22056 | | 7/1996 |
| WO | WO 96/13218 | | 9/1996 |
| WO | WO 97/00646 | | 1/1997 |
| WO | WO 97/00647 | | 1/1997 |
| WO | WO 97/10764 | | 3/1997 |
| WO | WO 97/24073 | | 7/1997 |
| WO | WO 97/24993 | | 7/1997 |
| WO | WO 98/27880 | | 7/1998 |
| WO | WO 99/03407 | | 1/1999 |
| WO | WO 99/03408 | | 1/1999 |
| WO | WO 99/03409 | | 1/1999 |
| WO | WO 99/12488 | | 3/1999 |
| WO | WO 99/23933 | | 5/1999 |
| WO | WO 99/40857 | | 8/1999 |
| WO | WO 99/40861 | | 8/1999 |
| WO | WO 99/51158 | | 10/1999 |
| WO | WO 99/66850 | | 12/1999 |
| WO | WO 00/24330 | | 5/2000 |
| WO | WO 00/24331 | | 5/2000 |
| WO | WO 00/36986 | | 6/2000 |
| WO | WO 00/41638 | | 7/2000 |
| WO | WO 00/47124 | | 8/2000 |
| WO | WO 00/53112 | | 9/2000 |
| WO | WO 01/17448 | | 3/2001 |
| WO | WO 01/54604 | | 8/2001 |
| WO | WO 02/07627 | | 1/2002 |
| WO | WO 02/067798 | | 9/2002 |
| WO | WO 02/080783 | | 10/2002 |
| WO | WO 02/080784 | | 10/2002 |
| WO | WO 02/080785 | | 10/2002 |
| WO | WO 02/080786 | | 10/2002 |
| WO | WO 02/080793 | | 10/2002 |
| WO | WO 02/080794 | | 10/2002 |
| WO | WO 02/080795 | | 10/2002 |
| WO | WO 02/080796 | | 10/2002 |
| WO | WO 02/080797 | | 10/2002 |
| WO | WO 02/080798 | | 10/2002 |
| WO | WO 02/080799 | | 10/2002 |
| WO | WO 02/081170 | | 10/2002 |
| WO | WO 03/061500 | | 7/2003 |
| WO | WO 03/090630 | | 11/2003 |
| WO | WO 03/101311 | | 12/2003 |
| WO | WO 2004/032776 | | 4/2004 |
| WO | WO 2004/032777 | | 4/2004 |
| WO | WO 2004/052221 | | 6/2004 |
| WO | WO 2004/073488 | | 9/2004 |
| WO | WO 2004/073490 | | 9/2004 |
| WO | WO 2004/073753 | | 9/2004 |
| WO | WO 2004/082495 | | 9/2004 |
| WO | WO 2004/098383 | | 11/2004 |
| WO | WO 2004/103156 | | 12/2004 |
| WO | WO 2005/004734 | | 1/2005 |
| WO | WO 2005/004735 | | 1/2005 |
| WO | WO 2005/110264 | | 11/2005 |
| WO | WO 2008/045348 | | 4/2008 |
| WO | WO 2008/045350 | | 4/2008 |

OTHER PUBLICATIONS

Peterson et al. "Comparison of Healing Process Following Ligation with Sutures and Bipolar Vessel Sealing" Surgical Technology International (2001).

"Electrosurgery: A Historical Overview" Innovations in Electrosurgery; Sales/Product Literature; Dec. 31, 2000.

Johnson et al. "Evaluation of a Bipolar Electrothermal Vessel Sealing Device in Hemorrhoidectomy" Sales/Product Literature; Jan. 2004.

E. David Crawford "Evaluation of a New Vessel Sealing Device in Urologic Cancer Surgery" Sales/Product Literature 2000.

Johnson et al. "Evaluation of the LigaSure Vessel Sealing System in Hemorrhoidectormy" American College of Surgeons (ACS) Clinicla Congress Poster (2000).

Muller et al., "Extended Left Hemicolectomy Using the LigaSure Vessel Sealing System" Innovations That Work, Sep. 1999.

Kennedy et al. "High-burst-strength, feedback-controlled bipolar vessel sealing" Surgical Endoscopy (1998) 12: 876-878.

Carus et al., "Initial Experience With the LigaSure Vessel Sealing System in Abdominal Surgery" Innovations That Work, Jun. 2002.

Heniford et al. "Initial Research and Clinical Results with an Electrothermal Bipolar Vessel Sealer" Oct. 1999.

Heniford et al. "Initial Results with an Electrothermal Bipolar Vessel Sealer" Surgical Endoscopy (2000) 15:799-801.

Herman et al., "Laparoscopic Intestinal Resection With the LigaSure Vessel Sealing System: A Case Report"; Innovations That Work, Feb. 2002.

Koyle et al., "Laparoscopic Palomo Varicocele Ligation in Children and Adolescents" Pediatric Endosurgery & Innovative Techniques, vol. 6, No. 1, 2002.

W. Scott Helton, "LigaSure Vessel Sealing System: Revolutionary Hemostasis Product for General Surgery"; Sales/Product Literature 1999.

LigaSure Vessel Sealing System, the Seal of Confidence in General, Gynecologic, Urologic, and Laparaoscopic Surgery; Sales/Product Literature; Apr. 2002.

Joseph Ortenberg "LigaSure System Used in Laparoscopic 1st and 2nd Stage Orchiopexy" Innovations That Work, Nov. 2002.

Sigel et al. "The Mechanism of Blood Vessel Closure by High Frequency Electrocoagulation" Surgery Gynecology & Obstetrics, Oct. 1965 pp. 823-831.

(56) References Cited

OTHER PUBLICATIONS

Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J.Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778 dated Oct. 31, 2000.
Int'l Search Report EP 98957771 dated Aug. 9, 2001.
Int'l Search Report EP 98958575.7 dated Sep. 20, 2002.
Int'l Search Report EP 04013772 dated Apr. 1, 2005.
Int'l Search Report EP 04027314 dated Mar. 10, 2005.
Int'l Search Report EP 04027479 dated Mar. 8, 2005.
Int'l Search Report EP 04027705 dated Feb. 3, 2005.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Sep. 28, 2005.
Int'l Search Report EP 05013895 dated Oct. 14, 2005.
Int'l Search Report EP 05016399 dated Jan. 5, 2006.
Int'l Search Report EP 05017281 dated Nov. 16, 2005.
Int'l Search Report EP 05019130.3 dated Oct. 18, 2005.
Int'l Search Report EP 05019429.9 dated May 6, 2008.
Int'l Search Report EP 05020665.5 dated Feb. 16, 2006.
Int'l Search Report EP 05020666.3 dated Feb. 17, 2006.
Int'l Search Report EP 05021197.8 dated Jan. 31, 2006.
Int'l Search Report EP 05021779.3 dated Jan. 18, 2006.
Int'l Search Report EP 05021780.1 dated Feb. 9, 2006.
Int'l Search Report EP 05021937.7 dated Jan. 13, 2006.
Int'l Search Report—extended—EP 05021937.7 dated Mar. 6, 2006.
Int'l Search Report EP 05023017.6 dated Feb. 16, 2006.
Int'l Search Report EP 06002279.5 dated Mar. 22, 2006.
Int'l Search Report EP 06005185.1 dated Apr. 18, 2006.
Int'l Search Report EP 06006716 dated Aug. 4, 2006.
Int'l Search Report EP 06008515.6 dated Jan. 8, 2009.
Int'l Search Report EP 06008779.8 dated Jun. 13, 2006.
Int'l Search Report EP 06014461.5 dated Oct. 20, 2006.
Int'l Search Report EP 06020574.7 dated Sep. 21, 2007.
Int'l Search Report EP 06020583.8 dated Jan. 30, 2007.
Int'l Search Report EP 06020584.6 dated Jan. 12, 2007.
Int'l Search Report EP 06020756.0 dated Feb. 5, 2007.
Int'l Search Report EP 06 024122.1 dated Mar. 19, 2007.
Int'l Search Report EP 06024123.9 dated Feb. 26, 2007.
Int'l Search Report EP 07 001480.8 dated Apr. 12, 2007.
Int'l Search Report EP 07 001488.1 dated May 29, 2007.
Int'l Search Report EP 07 009026.1 dated Sep. 12, 2007.
Int'l Search Report Extended—EP 07 009029.5 dated Jul. 12, 2007.
Int'l Search Report EP 07 009321.6 dated Aug. 17, 2007.
Int'l Search Report EP 07 010672.9 dated Oct. 1, 2007.
Int'l Search Report EP 07 013779.9 dated Oct. 18, 2007.
Int'l Search Report EP 07 014016 dated Jan. 28, 2008.
Int'l Search Report EP 07 015191.5 dated Dec. 19, 2007.
Int'l Search Report EP 07 015601.3 dated Dec. 6, 2007.
Int'l Search Report EP 07 020283.3 dated Jan. 16, 2008.
Int'l Search Report EP 07 021646.0 dated Jul. 9, 2008.
Int'l Search Report EP 07 021647.8 dated May 2, 2008.
Int'l Search Report EP 08 02692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report PCT/US98/18640 dated Dec. 17, 1998.
Int'l Search Report PCT/US98/23950 dated Dec. 29, 1998.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 3, 2001.
International Search Report PCT/US01/11224 dated Nov. 13, 2001.
Int'l Search Report PCT/US01/11340 dated Aug. 7, 2001.
Int'l Search Report PCT/US01/11420 dated Oct. 8, 2001.
Int'l Search Report PCT/US02/01890 dated Jul. 17, 2002.
Int'l Search Report PCT/US02/11100 dated Jul. 9, 2002.
Int'l Search Report PCT/US03/28534 dated Dec. 19, 2003.
Int'l Search Report PCT/US04/03436 dated Oct. 5, 2004.
Int'l Search Report PCT/US04/13273 dated Nov. 22, 2004.
Int'l Search Report PCT/US04/15311 dated Nov. 18, 2004.
Int'l Search Report PCT/US07/021438 dated Apr. 1, 2008.
Int'l Search Report PCT/US07/021440 dated Apr. 8, 2008.
Int'l Search Report PCT/US08/61498 dated Sep. 22, 2008.
Int'l Search Report EP 09 152267.2 Dated Jun. 15, 2009.
Int'l Search Report EP 09 152898.4 Dated Jun. 10, 2009.
Int'l Search Report PCT/US09/032690 dated Jun. 16, 2009.

* cited by examiner

APPARATUS, SYSTEM, AND METHOD FOR PERFORMING AN ENDOSCOPIC ELECTROSURGICAL PROCEDURE

BACKGROUND

1. Technical Field

The present disclosure relates to an apparatus, system, and method for performing an endoscopic electrosurgical procedure. More particularly, the present disclosure relates to an apparatus, system, and method for performing an endoscopic electrosurgical procedure that employs an endoscopic electrosurgical apparatus that includes an end effector assembly configured for use with various size access ports.

2. Description of Related Art

Electrosurgical apparatuses (e.g., electrosurgical forceps) are well known in the medical arts and typically include a handle, a shaft and an end effector assembly operatively coupled to a distal end of the shaft that is configured to manipulate tissue (e.g., grasp and seal tissue). Electrosurgical forceps utilize both mechanical clamping action and electrical energy to effect hemostasis by heating the tissue and blood vessels to coagulate, cauterize, seal, cut, desiccate, and/or fulgurate tissue As an alternative to open electrosurgical forceps for use with open surgical procedures, many modern surgeons use endoscopes and endoscopic electrosurgical apparatus (e.g., endoscopic forceps) for remotely accessing organs through smaller, puncture-like incisions. As a direct result thereof, patients tend to benefit from less scarring and reduced healing time, Typically, the endoscopic forceps are inserted into the patient through one or more various types of cannulas or access ports (typically having an opening that ranges from about five millimeters to about twelve millimeters) that has been made with a trocar; as can be appreciated, smaller cannulas are usually preferred.

Endoscopic forceps that are configured for use with small cannulas (e.g., cannulas less than five millimeters) may present design challenges for a manufacturer of endoscopic instruments.

SUMMARY

As noted above, smaller cannulas or access ports are usually preferred during an endoscopic procedure. However, because of size constraints associated with the cannula or access port, endoscopic forceps that are configured for use with the smaller cannulas may present design challenges for a manufacturer (e.g., designing an end effector assembly of an endoscopic forceps without compromising the integrity and/or functionality thereof).

Therefore, it may prove useful in the relevant arts to provide an endoscopic forceps that includes an end effector assembly that is configured for use with various types of cannulas or access ports including those that are less than five millimeters. With this purpose in mind, the present disclosure provides a bipolar forceps. The bipolar forceps includes a housing having a shaft that extends therefrom that defines a longitudinal axis therethrough. The housing includes a drive assembly disposed therein. The drive assembly is operable to reciprocate an actuation tube within the shaft. The bipolar forceps also includes an end effector assembly operatively connected to a distal end of the shaft having a pair of first and second jaw members biased in an open configuration. One or both of the first and second jaw members is pivotable about a living hinge from a first position wherein the jaw members are disposed in spaced relation relative to one another to a clamping position wherein the jaw members are moved closer to one another for grasping tissue. One or both of the jaw members includes a cam slot defined at a proximal end thereof. One or both of the jaw members is operatively connected to a distal end of the actuation tube via a cam pin that operatively engages a corresponding cam slot such that proximal reciprocation of the actuation tube cams at least one jaw member towards the other jaw member about the living hinge.

The present disclosure also provides a method for performing an electrosurgical procedure. The method includes the initial step of providing a bipolar forceps. The bipolar forceps includes a drive assembly operable to reciprocate an actuation tube. The bipolar forceps includes an end effector assembly having a pair of first and second jaw members biased in an open configuration. One or both of the first and second jaw members is pivotable about a living hinge from a first position wherein the jaw members are disposed in spaced relation relative to one another to a clamping position wherein the jaw members are moved closer to one another. One or both of the jaw members includes a cam slot defined at a proximal end thereof. One or both of the jaw members is operatively connected to a distal end of the actuation tube via a cam pin that operatively engages the cam slot. The method also includes the steps of: proximally actuating the drive assembly to move the actuation tube causing the cam pin to cam the first and second jaw members to pivot about the living hinge towards each other such that tissue is grasped therebetween; and applying electrosurgical energy to the jaw members such that a tissue seal may be effected therebetween.

BRIEF DESCRIPTION OF THE DRAWING

Various embodiments of the present disclosure are described hereinbelow with references to the drawings, wherein:

FIGS. 4A-4C are side, perspective views of an actuation rod configuration for use with the end effector assembly depicted in FIG. 1 in accordance with an embodiment of the present disclosure.

DETAILED DESCRIPTION

Detailed embodiments of the present disclosure are disclosed herein; however, the disclosed embodiments are merely exemplary of the disclosure, which may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure.

As noted above, it may prove useful in the arts to provide an electrosurgical apparatus that is suitable for use with various access ports, including but not limited to those that are greater than and/or less than five millimeters. With this purpose in mind, the present disclosure includes an electrosurgical forceps that includes an actuation tube operatively coupled to one or more jaw members associated with the end effector assembly of the electrosurgical forceps. The actuation tube configured to move the jaw members from an open to a closed configuration.

Figure 1:
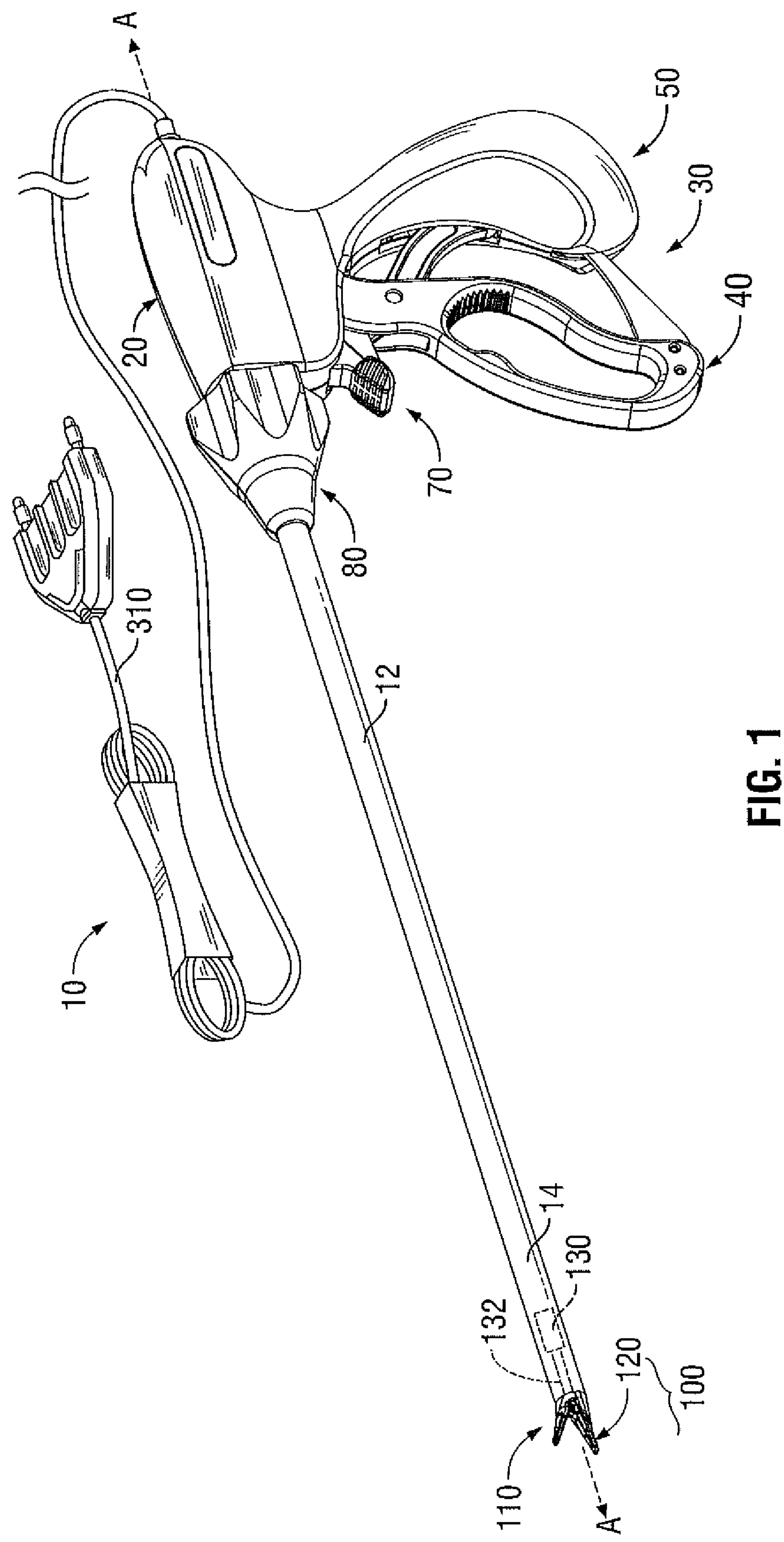
FIG. 1 is a perspective view of an endoscopic bipolar forceps including an end effector assembly, and electrosurgical generator in accordance with an embodiment of the present disclosure.
Figure 2:
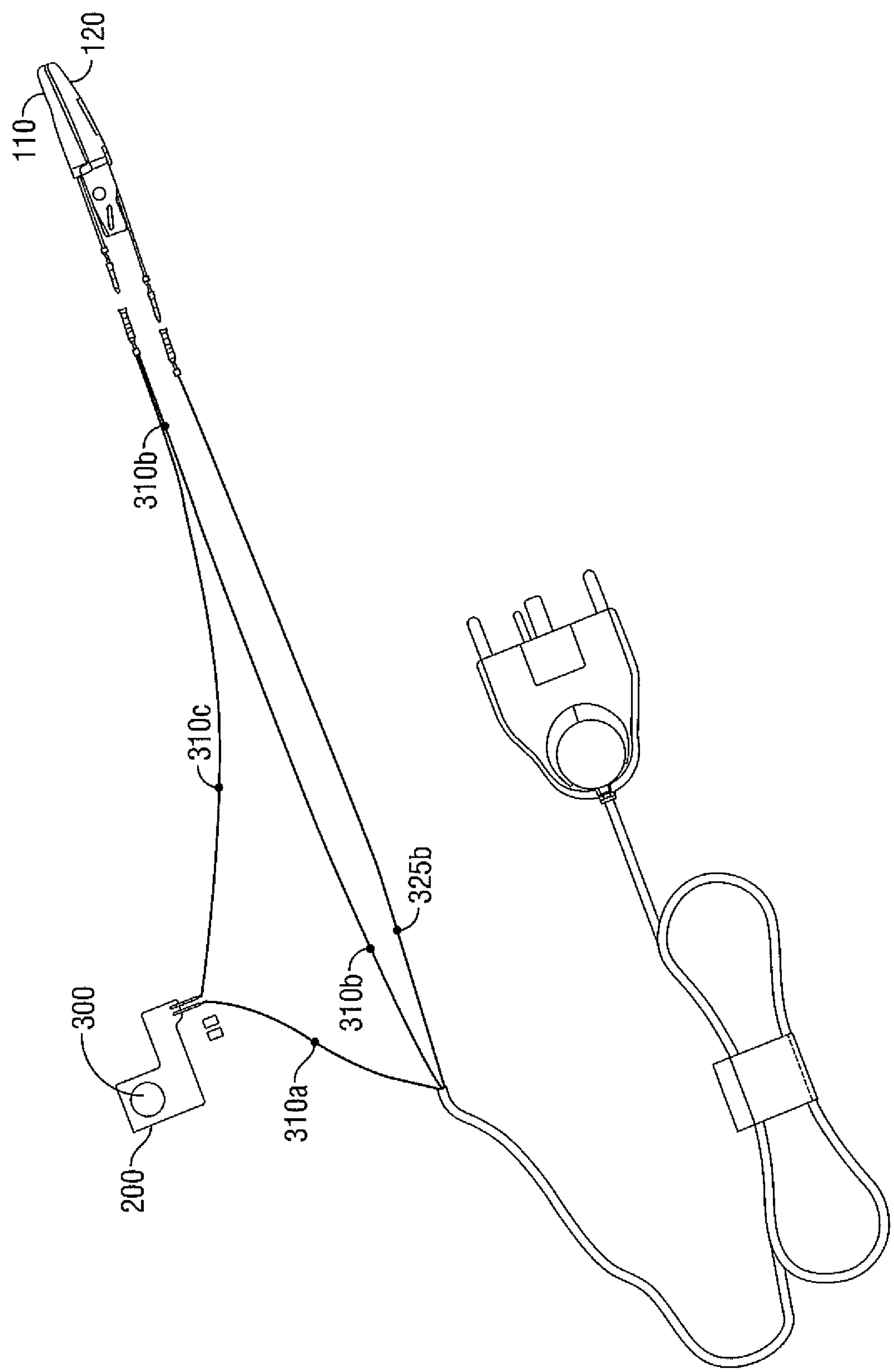
FIG. 2 is a schematic representation of an electrical configuration for connecting the endoscopic bipolar forceps to the electrosurgical generator depicted in FIG. 1.

With reference to FIG. 1 an illustrative embodiment of an electrosurgical apparatus (e.g., bipolar forceps 10) for performing an electrosurgical procedure is shown. Bipolar forceps 10 is operatively and selectively coupled to an electrosurgical generator (generator 200, see FIG. 2 for example) for performing an electrosurgical procedure. As noted above, an electrosurgical procedure may include sealing, cutting, cauterizing coagulating, desiccating, and fulgurating tissue; all of which may employ RF energy. Generator 200 may be configured for monopolar and/or bipolar modes of operation. Generator 200 may include or is in operative communication with a system (system 300, see FIG. 2 for example) that may include one or more processors in operative communication with one or more control modules that are executable on the processor. A control module (not explicitly shown) instructs one or more modules to transmit electrosurgical energy, which may be in the form of a wave or signal/pulse, via one or more cables (e.g., a cable 310) to one or both of the seal plates 118, 128. For a more detailed description of the generator 200 and/or system 300 reference is made to commonly owned U.S. application Ser. No. 10/427,832.

Figures 4A, 4B, 4C:
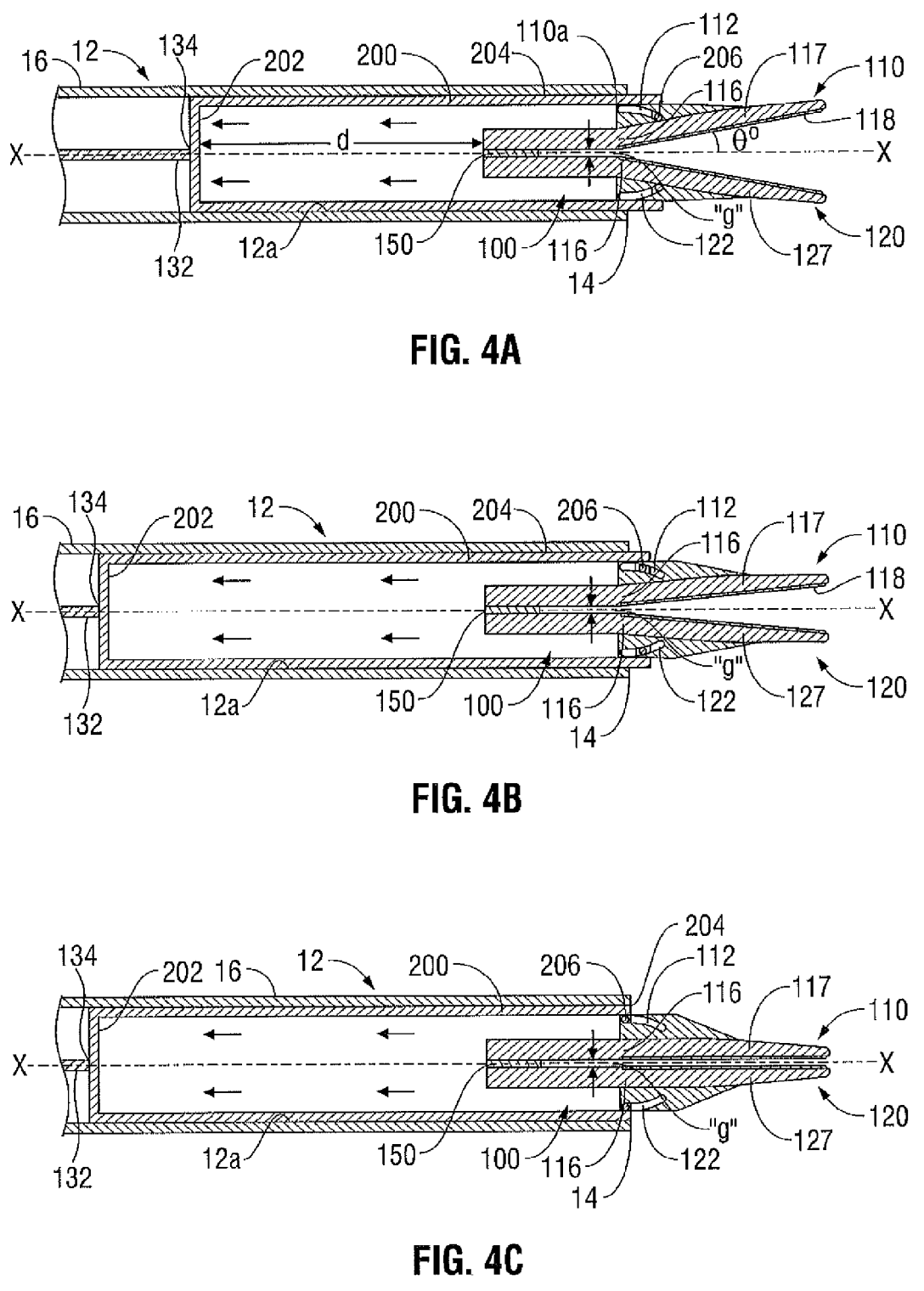

With reference again to FIG. 1, bipolar forceps 10 is shown for use with various electrosurgical procedures and generally includes a housing 20, a handle assembly 30, a rotating assembly 80, a trigger assembly 70, a drive assembly 130, and an end effector assembly 100 that operatively connects to the drive assembly 130 via an actuation tube 200 (see FIGS. 3-4C). End effector assembly 100 includes opposing jaw members 110 and 120 (FIG. 1) that mutually cooperate to grasp, seal and, in some cases, divide large tubular vessels and large vascular tissues. Although the majority of the figure drawings depict a bipolar forceps 10 for use in connection with endoscopic surgical procedures, the present disclosure may be used for more traditional open surgical procedures. For the purposes herein, the forceps 10 is described in terms of an endoscopic instrument; however, an open version of the forceps may also include the same or similar operating components and features as described below.

Forceps 10 includes a shaft 12, as described in greater detail below with reference to FIGS. 3A-4B, which has a distal end 14 configured in such a manner that a drive rod 132 of drive assembly 130 mechanically engages the end effector assembly 100 and a proximal end 16 which mechanically engages the housing 20. In the drawings and in the descriptions that follow, the term "proximal," as is traditional, will refer to the end of the forceps 10 which is closer to the user, while the term "distal" will refer to the end which is farther from the user.

With continued reference to FIG. 1, handle assembly 30 includes a fixed handle 50 and a movable handle 40. Fixed handle 50 is integrally associated with housing 20 and handle 40 is movable relative to fixed handle 50. Fixed handle 50 may include one or more ergonomic enhancing elements to facilitate handling, e.g., scallops, protuberances, elastomeric material, etc.

Movable handle 40 of handle assembly 30 is ultimately connected to drive assembly 130 including drive rod 132, which together mechanically cooperate to impart movement of actuation tube 200. Movement of actuation tube 200 causes jaw members 110 and 120 to move from an open position, wherein the jaw members 110 and 120 are disposed in spaced relation relative to one another, to a clamping or closed position, wherein the jaw members 110 and 120 cooperate to grasp tissue therebetween.

Rotating assembly 80 is operatively associated with the housing 20 and is rotatable approximately 180 degrees about a longitudinal axis "A-A" defined through shaft 12 (see FIG. 1).

Forceps 10 also includes an electrosurgical cable 310 that connects the forceps 10 to a source of electrosurgical energy, e.g., generator 200. Cable 310 is internally divided into cable leads 310*a*, 310*b*, 310*c*, and 325*b* (see FIG. 2) that are designed to transmit electrical potentials through their respective feed paths through the forceps 10 to the end effector assembly 100. More particularly, cable feed 325*b* connects through the forceps housing 20 and through the rotating assembly to jaw member 120. Lead 310*a* connects to one side of a switch (not shown) and lead 310*c* connects to the opposite side of the -switch such that upon activation of the switch energy is transmitted from lead 310*a* to 310*c*. Lead 310*c* is spliced with lead 310*b* that connects through the rotating assembly to jaw member 1 10.

For a more detailed description of handle assembly 30, movable handle 40, rotating assembly 80, electrosurgical cable 310 (including line-feed configurations and/or connections), and drive assembly 130 reference is made to commonly owned U.S. application Ser. No. 10/369,894.

Figure 3A:
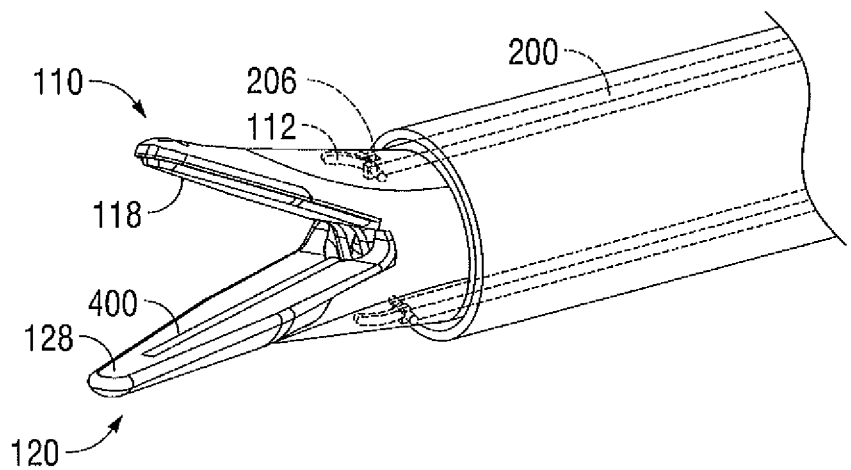
FIG. 3A is an enlarged, side view of the end effector assembly of FIG. 1.
Figure 3B:
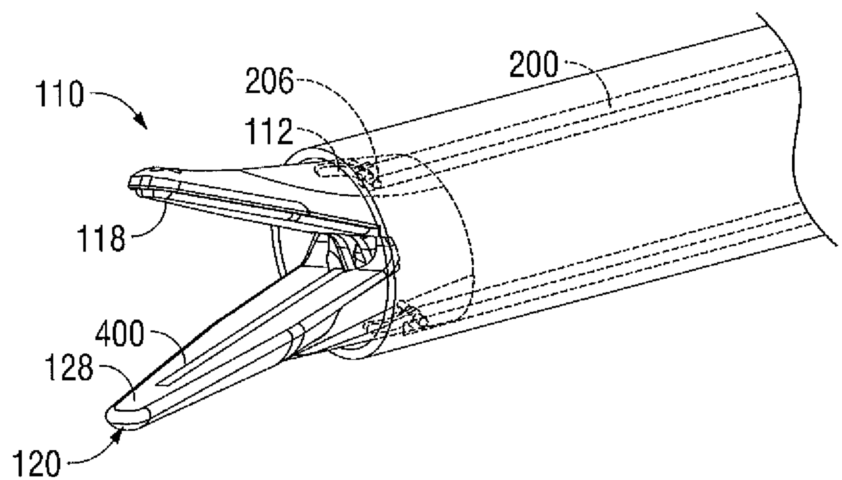
FIG. 3B is an enlarged, side view of the end effector assembly in accordance with an embodiment of the present disclosure.

Turning now to FIG. 3A shaft 12 includes distal end 14 operatively connected to end effector assembly 100 and actuation tube 200. Shaft 12 is configured to house drive assembly 130 and actuation tube 200 or portions thereof. At distal end 14 of shaft 12, jaw members 110 and 120, or portions thereof, are attached to an inner surface 12*a* (FIG. 4A) of shaft 12 via any suitable attaching means known in the art including but not limited to staking, welding, riveting, molding or overmolding.

Distal end 14 of shaft 12 is adapted to reciprocate actuation tube 200. Additionally, distal end 14 is dimensioned to allow jaw members 110 and 120 to flex, from an opened to closed configuration, during translation of actuation tube 200.

With continued reference to FIG. 4A, actuation tube 200 is shown. Actuation tube 200 may be manufactured from any suitable material including but not limited to plastic, metal, and the like. Actuation tube 200 may have any suitable geometric shape. In the illustrated embodiment, actuation tube 200 includes a proximal end 202 and distal end 204 defining a generally cylindrical structure, which includes one or more cam pins 206. Actuation tube 200 is configured for longitudinal translation with respect to each of jaw members 110 and 120, and spacer 150.

Actuation tube 200 is configured to fit within shaft 12, such that when drive rod 132 of drive assembly 130 is translated or "pulled" in a proximal direction, cam pins 206 of actuation tube 200 ride along a corresponding number of cam slots 112 and 122 located on the jaw members 110 and 120, respectively (two cam pins are shown in the drawings).

More particularly, proximal end 202 of actuation tube 200 is operatively connected to distal end 134 of drive rod 132, set back approximately a distance "d" from a proximal end of jaw members 110 and 120. A distal end 204 of actuation tube 200 is operatively connected to, and in mechanical communication with, one or more of the jaw members 110, 120 (both jaw members 110 and 120 are shown in mechanical communication with distal end 204). The distances that proximal end 202 of actuation tube 200 and distal end 134 of drive rod 132 may be set back from the proximal end of spacer 150 may vary. For example, distance "d" may be a distance that allows actuation tube 200 to translate distally and cause jaw members 110 and 120 to go from an open configuration to a closed configuration.

Distal end 204 or a portion thereof, of actuation tube 200 is configured for translation within shaft 12. Distal end 204 is operatively connected to one or more of cam slots 112 and 122 of jaw members 110 and 120, respectively, via mechanical engagement between one or more cam pins 206 (two cam pins 206 are shown).

Cam pins 206 extend laterally from an inside surface of actuation tube 200 and are configured to mechanically communicate with cam slots 112 and 122 to move the jaw members 110 and 120 from the open (FIG. 4A) to closed (FIG. 4C) configurations. Because jaw members 110 and 120 are in electrical communication with a source of electrosurgical energy, it may be useful to have cam pin 206, or portion thereof, manufactured from a non-conductive material. Cam pin 206 may be biased in a direction that is normal to the longitudinal axis "X". Having a cam pin 206 biased in such a manner may facilitate closing the jaw members 110, 120.

End effector assembly 100 includes opposing jaw members 110 and 120 that are fixedly attached to inner surface 12*a* of shaft 12. In embodiments, jaw members 110, 120 may be operatively and pivotably coupled to each other by way of a "V" link configuration and located within the distal end 14 of shaft 12 when the jaw members 110, 120 are in an initial open configuration (see FIG. 3B, for example). This jaw member configuration may facilitate a surgeon or user during the surgical procedure. That is, having the jaw members disposed within the distal end of the shaft may increase the "field of view" at the surgical site (e.g., area of tissue to be treated).

With reference again to FIG. 4A, a non-conductive spacer 150 disposed between the jaw members 110, 120 is configured to set a rear gap distance therebetween. Jaw members 110 and 120 are generally symmetrical and include similar component features which cooperate to effect the sealing and/or dividing of tissue. As a result, and unless otherwise noted, only jaw member 110 and the operative features associated therewith are described in detail herein, but as can be appreciated many of these features, if not all, apply to equally jaw member 120 as well.

Jaw member 110 includes an insulative jaw housing 117 and an electrically conductive seal plate 118 (hereinafter seal plate 118). The insulator 117 is configured to securely engage the electrically conductive seal plate 118. This may be accomplished by stamping, by overmolding, by overmolding a stamped electrically conductive sealing plate and/or by overmolding a metal injection molded seal plate. All of these manufacturing techniques produce an electrode having a seal plate 118 that is substantially surrounded by the insulating substrate. Within the purview of the present disclosure, jaw member 110 may include a jaw housing 117 that is integrally formed with a seal plate 118.

Jaw member 120 includes a similar structure having an outer insulative housing 127 that is overmolded to capture seal plate 128.

Jaw member 110 includes a living hinge located at a proximal end 110*a* thereof. Proximal end 110*a* of jaw member 110 is bent near a distal end of spacer 150, such that a living hinge 116 is formed. Hinge 1 16 is bent in such a manner that an angle θ is formed relative to the longitudinal axis "X", as best seen in FIG. 4A. The angle θ may range from about 0° to about 90°. Other angles θ of the jaw member 110 relative to the longitudinal axis "X" are contemplated and within the scope of the present disclosure.

Cam slot 112 is located on a surface of jaw member 110 and interacts with cam pin 206 of actuation tube 200, as shown in FIGS. 4A-4C. Cam slot 112 may be formed on jaw member 110 by any of the previously described stamping and/or overmolding manufacturing techniques and may be formed by other suitable methods, e.g., drilling, etching, or machining, and so on. Cam slot 112 is configured in a manner such that when cam pin 206 rides along cam slot 112 jaw member 110 pivots about living hinge 116. While cam slot 112 is depicted as having a generally concave/convex or arcuate structure, cam slot 112 may have any suitable structure that will allow jaw member 110 to function as described above. Cam slot 112 may be formed on a side surface (not explicitly shown), of jaw member 110. This, of course, will depend on the contemplated uses by the manufacturer.

Cam slot 122, operatively formed on jaw member 120, is configured and operable in a manner that is the same as or substantially similar to cam slot 112 of jaw member 1 10.

Spacer 150 may be integrally formed with one or both of the jaw members 110 and 120, via any of the previously described manufacturing techniques, e.g., stamping and/or overmolding. Alternatively, spacer 150 may be a separate member operatively connected to each of the jaw members 110 and 120, or operatively connected to a distal end 14 of shaft 12. As mentioned above, spacer 150 may be configured to define a gap distance "g" between jaw members 110 and 120 (FIGS. 4A-4C). Gap distance may be any suitable distance; however, in one embodiment, gap distance "g" may be between about 0.001 inches and 0.006 inches. Gap distances less than 0.001 inches and greater than 0.006 inches are within the purview of the present disclosure. Spacer 150 is configured to isolate the electrically conductive seal surfaces 118 and 114 of jaw members 110 and 120, respectively. Spacer 150 may be formed from any suitable material including but not limited plastics, metals, and the like. Spacer 150 may be either conductive, non-conductive, or a combination thereof.

Spacer 150 may include a knife slot (not explicitly shown) defined therethrough configured to receive a knife blade, or portion thereof, and allow translation of the knife blade therethrough. The knife slot may extend distally from spacer 150 and substantially align with a knife slot 180 located on one or more of the jaw members 110 and 120 (FIG. 3A)

In use, prior to sealing tissue, jaw members 110 and 120 are initially be biased in an open configuration, each disposed at an angle θ relative to the longitudinal axis "X", and actuation tube 200 may be set back at a distance "d" from the proximal end of each jaw member 110, 120 (FIG. 4A). When tissue is ready to be grasped for treating, a user positions tissue between jaw members 110 and 120, and squeezes handle 40 which, in turn, causes drive rod 132 of drive assembly 103 to translate proximally. As drive rod 132 is translated or "pulled" proximally, actuation tube 200 translates proximal, which, in turn, causes cam pins 206 to ride along cam slots 112 and 122 of jaw members 110 and 120, respectively. As actuation tube 200 moves proximally, jaw members 110 and 120 will flex radially inwardly, about living hinge 116, toward each other and the longitudinal axis "X" (FIG. 4B). When proximal end 202 of actuation tube 200 has moved approximately a distance "d", jaw members 110 and 120 will be substantially parallel to each other and the longitudinal axis "X", separated approximately by a gap distance "g" causing tissue to be grasped therebetween (FIG. 4C). After tissue is grasped between jaw members 110 and 120, electrosurgical energy may be transmitted to the jaw members 110 and 120 effecting a tissue seal therebetween, or other suitable tissue effect.

Upon completion of effecting a tissue seal, a user releases handle 40, which, in turn, causes drive rod 132 of drive rod assembly 130 to translate distally. As drive rod 132 is translated or "pushed" distally, actuation tube 200 translates distally, which, in turn, causes cam pins 206 to ride along cam slots 112 and 122 of jaw members 110 and 120, respectively. As actuation tube 200 moves distally, jaw members 110 and 120 will flex radially outward, about living hinge 116, away from each other and the longitudinal axis "X" (FIG. 4B). When proximal end 202 of actuation tube 200 has moved approximately a distance "d", jaw members 110 and 120, returning to their initial open configuration, will again be disposed at an angle θ relative to the longitudinal axis "X" (FIG. 4A).

Figure 5:
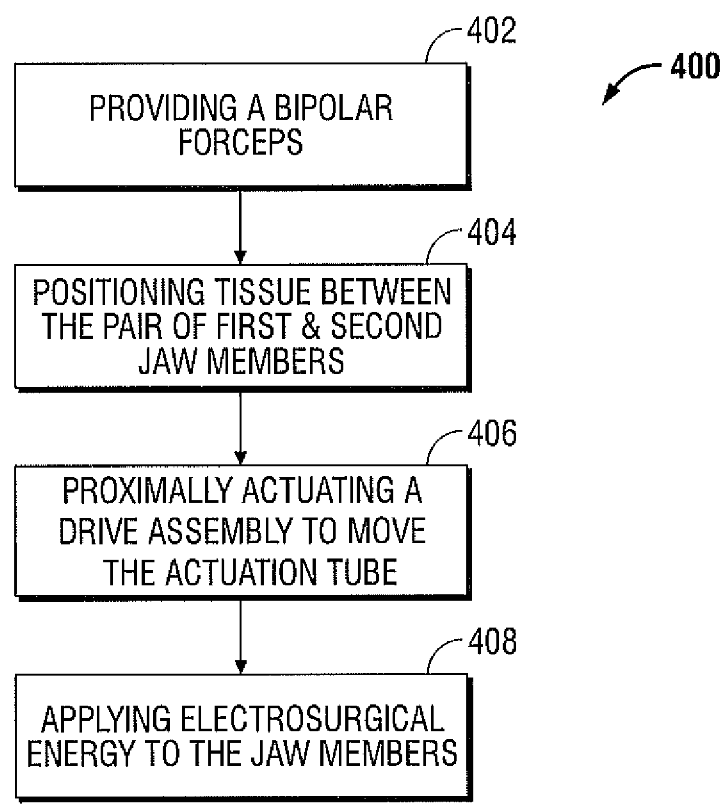
FIG. 5 is a flowchart illustrating a method for performing an electrosurgical procedure in accordance with an embodiment of the present disclosure.

The present disclosure also provides a method 400 for performing an electrosurgical procedure. As illustrated in FIG. 5, at step 402 a bipolar forceps is provided. At step 404, tissue is positioned between the pair of first and second jaw members such that a tissue seal may be effected. At step 406, the drive assembly is actuated to move the actuation tube causing the cam pin to cam the first and second jaw members to pivot about the living hinge and cam towards each other such that tissue is grasped therebetween. And at step 408, electrosurgical energy is applied to the jaw members such that a tissue seal may be effected therebetween.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A bipolar forceps, comprising:

a housing having a shaft that extends therefrom that defines a longitudinal axis therethrough, the housing including a drive assembly operable to reciprocate an actuation tube within the shaft; and an end effector assembly operatively connected to a distal end of the shaft having a pair of first and second jaw members biased in an open configuration, at least one of the first and second jaw members pivotable about a living hinge from a first position wherein the jaw members are disposed in spaced relation relative to one another to a clamping position wherein the jaw members are moved closer to one another for grasping tissue, at least one of the jaw members including a cam slot defined at a proximal end thereof at a position that is distal relative to the living hinge, wherein the at least one jaw member is operatively connected to a distal end of the actuation tube via a cam pin that operatively engages the cam slot such that proximal reciprocation of the actuation tube moves the cam pin proximally within the cam slot and cams the at least one jaw member towards the other jaw member about the living hinge, wherein the jaw members are housed within the distal end of the shaft when the jaw members are in the closed configuration.

2. The bipolar forceps according to claim 1, wherein the jaw members are electrically isolated from each other via a non-conductive spacer disposed between the proximal ends of the jaw members.

3. The bipolar forceps according to claim 2, wherein the spacer provides a gap distance from about 0.001 inches to about 0.006 inches between the jaw members when disposed in the clamping position.

4. The bipolar forceps according to claim 2, wherein the spacer provides a gap distance that is greater than 0.006 inches between the jaw members when disposed in the clamping position.

5. The bipolar forceps according to claim 1, wherein the cam slot of the at least one jaw member is overmolded on the at least one jaw member.

6. The bipolar forceps according to claim 1, wherein the cam slots of the at least one jaw member is arcuate.

7. The bipolar forceps according to claim 1, wherein the drive assembly includes an actuation rod coupled to the actuation tube to actuate the jaw members.

8. The bipolar forceps according to claim 1, wherein each jaw member includes an outer insulative housing that is overmolded to capture a sealing plate for engaging tissue, the outer insulative housing configured to include the cam slot at a proximal end thereof.

9. The bipolar forceps according to claim 1, wherein each jaw member includes an outer insulative housing and a sealing plate that are integrally formed together for engaging tissue, the outer insulative housing configured to include the cam slot at a proximal end thereof.

10. The bipolar forceps according to claim 1, wherein the first and second jaw members are both pivotable about a living hinge from the first position to the clamping position, the first and second jaw members each including a cam slot defined therein, each of the cam slots of the first and second jaw members operably coupled to the distal end of the actuation tube via corresponding cam pins such that proximal reciprocation of the actuation tube moves the cam pins proximally within the cam slots and cams the first and second jaw members toward one another about the respective living hinges.

* * * * *